United States Patent
Wiley (10) Patent No.: US 8,172,802 B2
(45) Date of Patent: May 8, 2012

(54) INTRAVASCULAR NEEDLE AND CATHETER ASSEMBLY

(75) Inventor: Christopher W. Wiley, Hanover, NH (US)

(73) Assignee: Dartmouth-Hitchcock Clinic, Lebanon, NH (US)

(*) Notice: Subject to any disclaimer, the term of this patent is extended or adjusted under 35 U.S.C. 154(b) by 0 days.

(21) Appl. No.: 12/623,873

(22) Filed: Nov. 23, 2009

(65) Prior Publication Data

US 2010/0137804 A1 Jun. 3, 2010

Related U.S. Application Data

(60) Provisional application No. 61/117,273, filed on Nov. 24, 2008.

(51) Int. Cl.
*A61M 5/178* (2006.01)
*A61M 25/00* (2006.01)

(52) U.S. Cl. ......... 604/164.06; 604/164.01; 604/170.03; 604/523

(58) Field of Classification Search .............. 604/164.06, 604/168.01, 107.03, 164.01, 170.03, 264, 604/922, 6.16, 17, 900, 523
See application file for complete search history.

(56) References Cited

U.S. PATENT DOCUMENTS

| | | |
|---|---|---|
| 4,645,491 A | 2/1987 | Evans |
| 4,699,612 A | 10/1987 | Hamacher |
| 4,808,158 A | 2/1989 | Kreuzer et al. |
| 5,100,390 A | 3/1992 | Lubeck et al. |
| 5,290,246 A | 3/1994 | Yamamoto et al. |
| 5,368,573 A | 11/1994 | Andrew |
| 5,407,441 A | 4/1995 | Greenbaum |
| 5,478,328 A * | 12/1995 | Silverman et al. ............ 604/272 |
| 5,538,009 A | 7/1996 | Byrne et al. |
| 5,601,559 A | 2/1997 | Melker et al. |
| 5,649,911 A | 7/1997 | Trerotola |
| 5,843,048 A | 12/1998 | Gross |
| 5,868,699 A | 2/1999 | Woodruff et al. |
| 5,951,528 A | 9/1999 | Parkin |
| 6,273,877 B1 | 8/2001 | West et al. |
| 6,554,809 B2 | 4/2003 | Aves |
| 6,702,790 B1 | 3/2004 | Ross et al. |
| 7,002,098 B2 | 2/2006 | Adams |
| D561,338 S | 2/2008 | Blanco |

FOREIGN PATENT DOCUMENTS

DE 36 43 235 C1 11/1987

(Continued)

*Primary Examiner* — (Jackie) Tan-Uyen T. Ho
*Assistant Examiner* — Leah Stohr
(74) *Attorney, Agent, or Firm* — William A. Loginov, Esq.; Loginov & Associates, PLLC (57) ABSTRACT

An intravascular needle and catheter arrangement that ensures flashback is indicated after the catheter is safely inserted through the needle puncture in the vascular wall and emplaced into the vessel. This placement location, at which flashback first occurs is sufficient to begin threading the catheter without risk of over-insertion or under-insertion. The catheter overlies a needle having a distal tip that defines a point. The needle tip includes an enclosed distal-most end and a port located along at least one of the proximal portion of the point and an adjacent cylindrical sidewall of the needle. The distal end of the catheter exposes the port for entry of blood from a vessel thereinto only after the distal end of the catheter has entered sufficiently into the interior of the vessel. An opposing second side of the tip defines a curved surface that prevents puncturing of the back vessel wall.

14 Claims, 8 Drawing Sheets

FOREIGN PATENT DOCUMENTS

| | | |
|---|---|---|
| DE | 94 00 470 | 3/1994 |
| DE | 195 12 607 A1 | 10/1996 |
| DE | 298 07 150 | 8/1998 |
| DE | 103 00 452 A1 | 10/2003 |
| EP | 0 824 932 A2 | 2/1998 |
| WO | WO 03089035 A1 | 10/2003 |

* cited by examiner

INTRAVASCULAR NEEDLE AND CATHETER ASSEMBLY

RELATED APPLICATIONS

This application claims the benefit of U.S. Provisional Patent Application Ser. No. 61/117,273, filed Nov. 24, 2008, entitled IMPROVED INTRAVASCULAR NEEDLE AND CATHETER ASSEMBLY, by Christopher W. Wiley, the entire disclosure of which is herein incorporated by reference.

FIELD OF THE INVENTION

This invention relates to needle and catheter arrangements for insertion of intravenous and arterial catheters.

BACKGROUND OF THE INVENTION

One of the most commonly performed invasive procedures in modern medicine is the insertion of an intravenous (IV) or arterial catheter. However these procedures require substantial skill for success, and even experienced and skilled practitioners have exhibited significant failure rates. This results in considerable pain and anxiety for the patient, who may have to endure multiple attempts to insert the catheter. Experienced clinicians report that nearly every patient they encounter vividly recalls having suffered failed IV or arterial insertions in the past.

Most insertion failures appear to occur at a discrete point in this multi-step procedure. That is, the attempt to thread the catheter after the vessel has been punctured by the needle, and flashback of blood has occurred. Beginners often fail to appreciate that when the flashback of blood occurs for the clinician to observe, the needle tip (and orifice) are in the vein or artery, but the catheter tip, which overlies the needle, has not yet entered the vessel. Rather, the catheter tip may still be proximal of the vessel. This is because blood begins to enter the needle lumen under pressure (and hence flashes back at the proximal end of the needle) as soon as the needle lumen is placed in fluid communication with the bloodstream.

Figure 1:
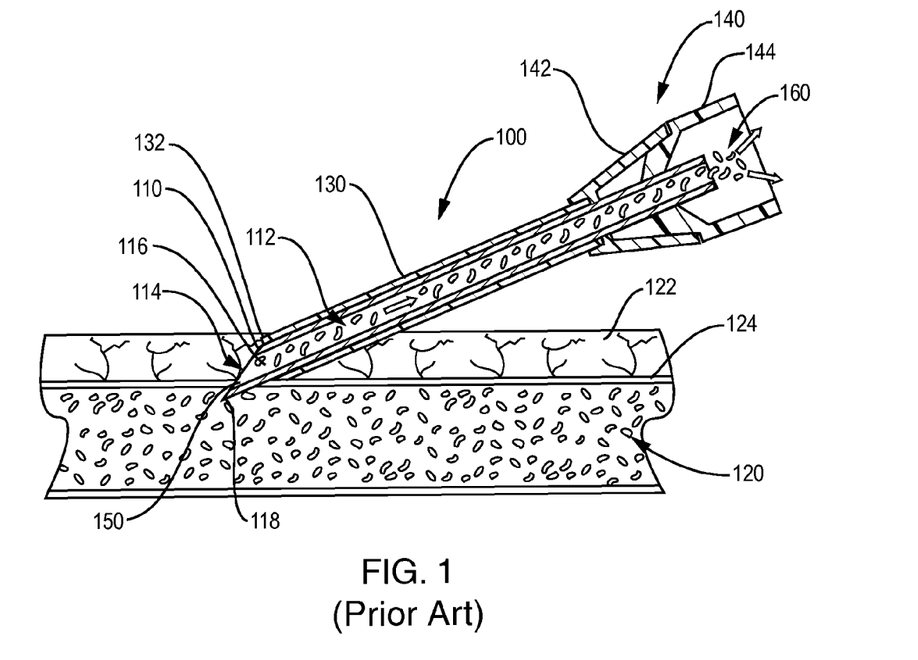
FIG. 1, already described, is a side cross section of a conventional insertion needle and catheter arrangement shown during flashback of blood from an exemplary vessel prior to full insertion of the catheter tip thereinto.

By way of further illustration of this undesirable outcome, reference is made to FIG. 1, which depicts a typical needle and catheter arrangement 100 according to the prior art. The arrangement 100 includes a hollow metallic (typically surgical stainless steel) insertion needle 110 with a lumen 112 of appropriate size/diameter for the blood vessel 120 into which it is inserted (For example, needle sizes 14 gauge (G), 16 G, 18 G, 20 G, 22 G or 24 G). The distal end of the needle includes a conventional sharp, beveled, chisel-like tip 114 with an open orifice 116 that extends proximally into the lumen directly from the angled cylindrical orifice edge. This tip includes a distal point 118 that is quite sharp and enables piercing of the skin layer 122 and vascular wall 124 as shown with minimal discomfort for the patient. Overlying the needle 110, proximal of the tip 114 is a closely conforming catheter 130 constructed from a biocompatible polymer of conventional design. The distal end 132 of the catheter ends proximally of the angled tip 114, forming a small-diameter step that normally passes into the puncture hole created by the tip 114. The proximal end of the arrangement 110 typically includes an assembly with a distal portion that defines a fitting 142 interconnected with the catheter 130 and a proximal portion 144 that is interconnected with the needle. The two portions 142 and 144 can be withdrawn axially from each other so as to withdraw the needle 110 proximally from within the catheter lumen, while maintaining or advancing the catheter 130 distally with respect to the vessel 120 so as to thread and implant the catheter fully into the vessel.

As shown in FIG. 1, the needle tip 114 has been inserted by the clinician into the vessel 120 and the now-open path between a distal-most portion 150 of the tip orifice 116 and the bloodstream causes the flashback of blood through the needle lumen 112, which is visible in a flash chamber 160 at the proximal end. However no portion (or substantially no portion) of the catheter's distal end 132 has entered the vessel 120. Thus, an inexperienced or inattentive clinician may attempt to thread the catheter immediately upon such flashback. This premature threading generally causes the clinician to blow the insertion, because the catheter tip 132 pushes the pliant vessel 120 away from, and off of, the needle as the catheter is driven distally in an attempt to implant it in the vessel.

Figure 2:
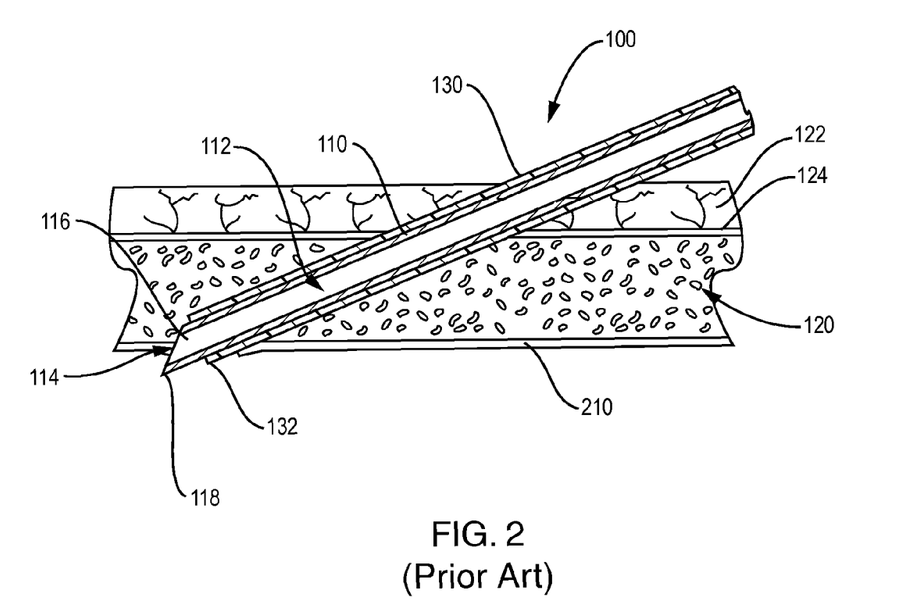
FIG. 2, already described, is a side cross section of the insertion needle and catheter arrangement of FIG. 1 shown with its tip damaging the back wall of the vessel due to over-insertion thereof.

More experienced practitioners, conversely, are aware that, following flashback, the entire needle/catheter arrangement 100 should be inserted an additional 2 mm (more or less) before catheter threading is attempted. Unfortunately, as shown in FIG. 2, during this additional-distance insertion, the sharp, beveled point 118 on the distal tip of the needle 110 often penetrates the opposite or back wall 210 of the vessel 120 resulting in failure and a painful hematoma.

U.S. Pat. No. 5,649,911, entitled INTRAVENOUS CATHETER AND DELIVERY SYSTEM, by Trerotola provides a solid, beveled needle tip joined to a straight cylindrical body with a side hole proximally spaced from, but near the tip. The hole is carried on the needle body and the adjacent overlying catheter wall, near its distal end. This hole enables flashback to occur after the catheter has fully penetrated the vessel, so that it can be threaded without risk of non-penetration. However, the use of a solid tip dictates that the needle be inserted a significant distance into the vessel before any flashback occurs. This degree of insertion may, in fact be excessive. In addition, the tip is constructed with the traditional bevel, having a point residing in line with the sidewall. In other words, the tip and point are simply extensions of the bottom side of the cylindrical needle shaft, and thus the structure of the needle still invites over-insertion as set forth in FIG. 2 above. The risk of over-insertion is, in fact enhanced by the relatively proximal placement of the side hole. Moreover, the traditional beveled tip does nothing to reduce the damage potential from an over-penetrating insertion.

It is, thus desirable to provide an intravascular needle and catheter arrangement that provides flashback at the point in which the catheter is sufficiently inserted into the vessel. It is also desirable to provide a needle that reduces the risk of damage to the vessel from over-insertion of the needle.

SUMMARY OF THE INVENTION

This invention overcomes the disadvantages of the prior art by providing an improved intravascular needle and catheter arrangement for use in arterial and intravenous (IV) insertions that ensures flashback is indicated after the catheter is safely inserted through the needle puncture in the vascular wall and emplaced into the vessel. This placement location, at which flashback first occurs is sufficient to begin threading the catheter without risk of over-insertion or under-insertion. The geometry of the needle tip, while providing a sharpened point that minimizes insertion pain and increases the chance of success, also reduces the chance of damage to the back wall of the vessel, should over-insertion occur. In an illustrative embodiment, the catheter compromises a flexible polymeric shaft that flexibly overlies a needle having a distal tip that defines a point. The needle tip includes an enclosed distal-most end and a port located along at least one of the proximal portion of the point and an adjacent cylindrical sidewall of the needle. The distal end of the catheter is constructed and arranged so as to expose the port for entry of blood from a vessel thereinto only after the distal end of the catheter has entered sufficiently into the interior of the vessel for threading. The point is disposed at or near a central axis of the needle shaft, with the port disposed on a first side of the tip and an opposing second side of the tip defining a generally curved surface, or heel, that allows the tip to be deflected along the back wall of the vessel in the event of over-insertion, rather than puncturing it.

In illustrative embodiments, the first tip side adjacent the port can define a flattened surface. The port can define a slot formed along the flattened surface and/or the adjoining cylindrical side of the needle. Alternatively, the port can be formed along only the cylindrical side, adjacent to the tip. The catheter can include a conforming slot that allows passage of blood through the needle port and into the inner lumen for flashback at a proximal flashback chamber that is interconnected with the needle and removably connected to a luer or other proximal catheter fitting. Where the port extends onto the needle tip, the catheter can include a distal end that tapers to cover and conform with a proximal portion of the tip, and having a catheter distal edge approximately aligned with the distal edge of the port. The tip can be hollow or solid. It can be formed unitarily with the needle shaft—by, for example swaging, welding and/or soldering. Alternatively, the tip can be an attached component formed from metal, a durable polymer or another appropriate material.

A medical treatment procedure employing the above-described needle is also provided. This procedure allows for detection of full insertion via the observed flashback and minimizes potential damage to the inner vessel wall opposite the puncture side of the vessel based upon the curved/rounded heel described herein.

BRIEF DESCRIPTION OF THE DRAWINGS

The invention description below refers to the accompanying drawings, of which.

DETAILED DESCRIPTION

Figure 3:
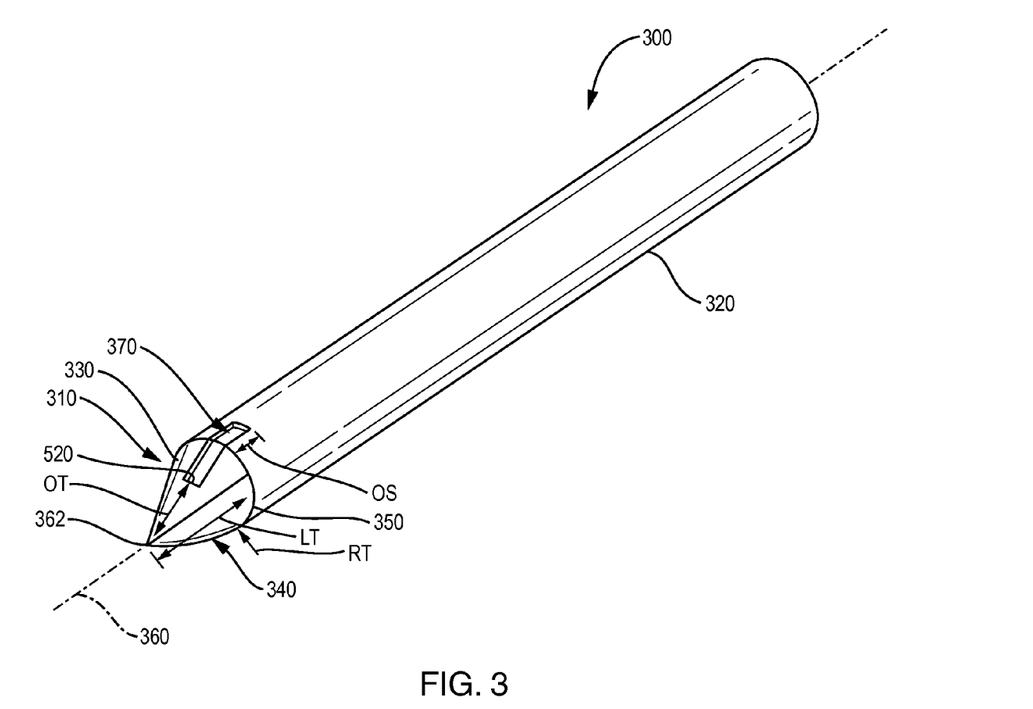
FIG. 3 is a perspective view of an insertion needle according to an illustrative embodiment including a tip having a centered point with a proximally positioned port located along both the tip and adjacent shaft side to help prevent flashback prior to full insertion and an opposing second side shaped with a rounded surface to minimize damage due to over-insertion.

FIG. 3 shows an insertion needle 300 having a distal tip according to an illustrative embodiment. The tip 310 is formed on the distal end of the needle shaft 320. The shaft 320 in this embodiment defines a cylinder sized in an appropriate diameter (14-24 G, for example) for use in an arterial or IV insertion application. The needle is constructed from a suitable metal or other biocompatible material, such as stainless steel. The tip 310 can be formed by a variety of techniques as described above. For example, the tip can be built up using weldments and/or solder on the end of a cylindrical needle shaft. The shaft end can also be formed into the depicted tip using a swaging or similar plastic deformation technique. The tip can alternatively comprise a separate unit that is affixed to the end of the cylindrical shaft using appropriate attachment techniques. The tip includes a first (upper) side 330 defining a flattened tapered surface and an opposing second (bottom) surface 340 defining a curved heel, both of which are described further below. Note, by "opposing" herein it is typically meant diametrically opposed. The tip 310 in this embodiment interconnects with the straight, cylindrical shaft section 320 at a relatively circular junction 350 residing in a plane that is approximately perpendicular to the longitudinal (axis of elongation) axis 360 taken along the center (cross-sectional center/centroid) of the shaft 320. Note, in alternate embodiments, the shaft can be non-linear along at least a portion of its length and the tip need not join the shaft at a planar, circular junction, but at junction giving a different geometry.

Notably, the tip 310 includes a sharp point 362 that, in this embodiment resides approximately within the axis 360. It is contemplated that the point may reside below or above this axis in alternate embodiment. However, the point 362 should be located so as to generate an upwardly sloping/curving heel 340 capable of operating to reduce potential damage to the vascular wall in accordance with the principles of the invention as will be described below. In addition, the novel tip of this embodiment is enclosed at its distal end, and provides an orifice or port 370 that is located proximally from the point at an offset distance OT. This distance is highly variable, but can be at least ½ the total length LT of the tip in various embodiments. The port may be located exclusively on the tip 310, or, as shown can extend onto the distal portion of the shaft 320. In this embodiment, the distance of extension OS of the port 370 onto the shaft 320 is highly variable. For example the distance OT can be equal to OS. In general, the overall length of the port 370 in a typical embodiment can be between 1 and 4 millimeters, but this dimension is highly variable. As described in detail below, the placement of the port 370 with respect to the tip is expressly contemplated to ensure that flashback occurs after the overlying catheter has passed through the puncture in the vascular wall, and the practitioner can, thus, be ensured that threading of the catheter will result in a successful procedure. The catheter is shown in further detail as part of the overall insertion needle and catheter arrangement in FIGS. 4-6.

Figure 4:
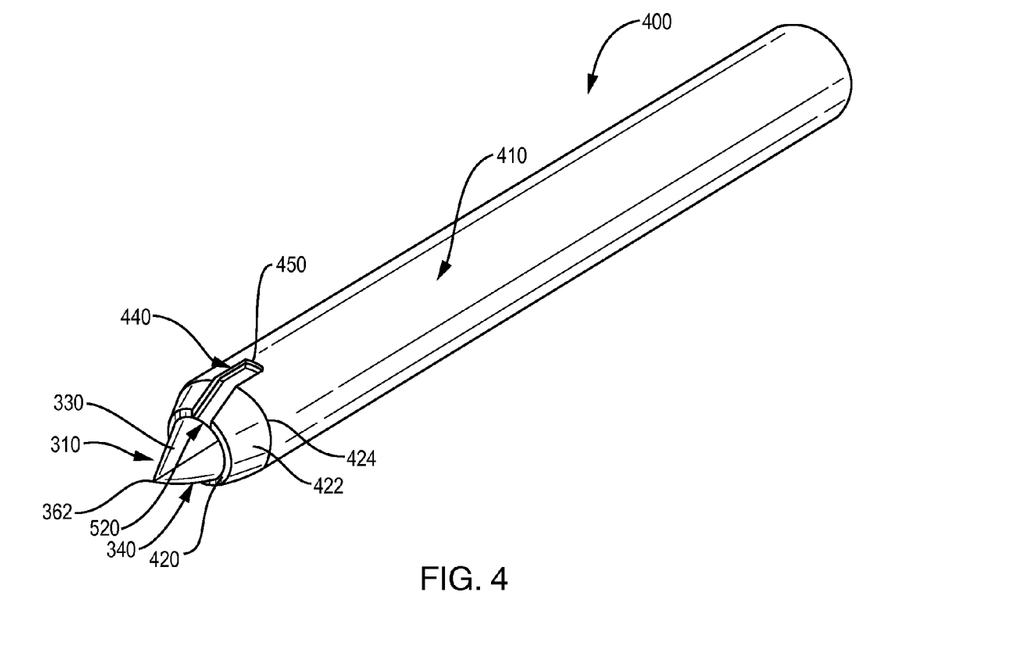
FIG. 4 is a perspective view of a catheter and needle arrangement according to an illustrative embodiment, employing the needle of FIG. 3 and including an overlying catheter having a distal end that extends into a taper on the needle tip and includes a slot approximately aligned with the needle port.
Figure 5:
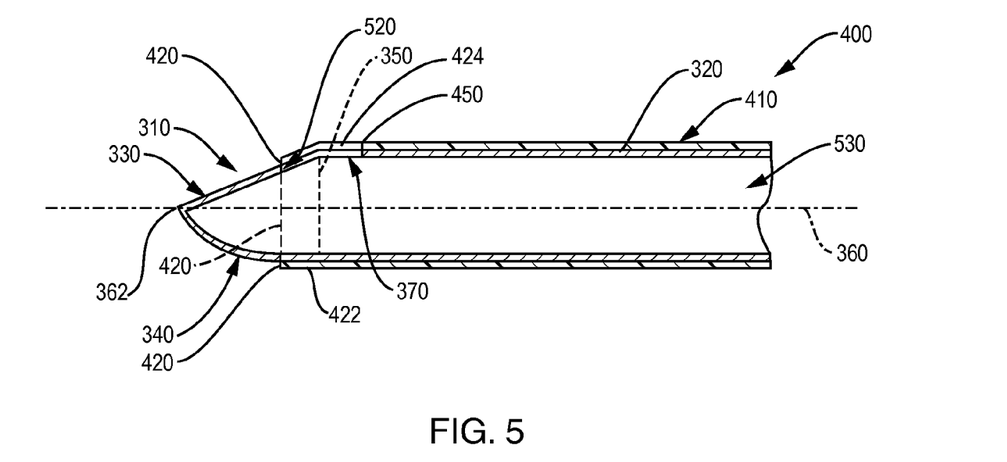
FIG. 5 is a partial side cross section of the distal portion of the needle and catheter arrangement of FIG. 4.
Figure 6:
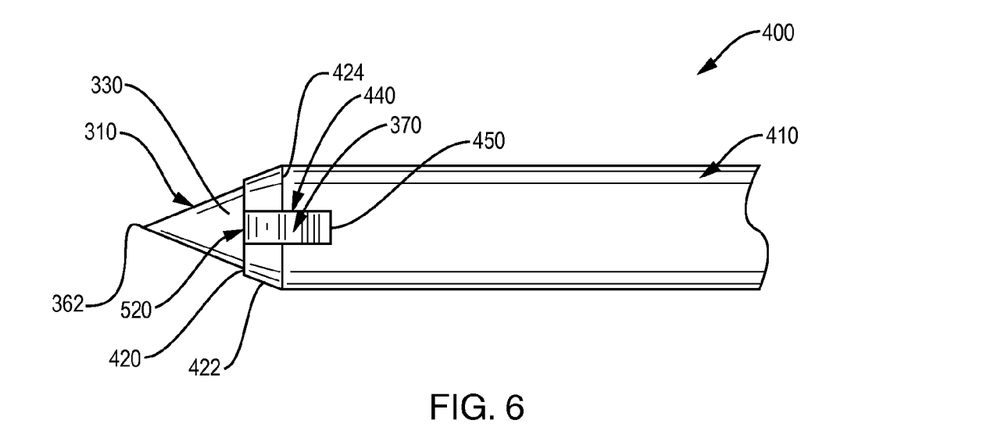
FIG. 6 is a partial top view of the distal portion of the needle and catheter arrangement of FIG. 4.

As shown in FIGS. 4-6, a flexible polymeric catheter 410 having an essentially conventional wall thickness, and being constructed from conventional materials snugly, but slidably overlies the needle shaft 320 to provide the complete needle and catheter arrangement 400. In this embodiment, the needle tip 310 is partially exposed at the point 362, and proximally therefrom, to enable puncture of the intervening skin layers and vascular tissue during insertion. Notably, the distal end 420 of the catheter 410 is part of a beveled surface 422 that extends past the shaft-to-tip junction 350 at an overlying circular joint 424. The beveled surface extends distally to its distal end 420, which is aligned approximately with the distal edge 520 of the port 370. In various embodiments, the catheter distal edge can be slightly distal or slightly proximal of the port's distal edge 520.

The catheter defines a notch 440 that is aligned over the needle port 370. This notch extends from corners on the distal end 420 to a proximal edge 450. This notch 440 allows blood from the vessel to enter the needle lumen 530 unobstructed by the catheter tip during flashback.

As viewed particularly in FIG. 5, the heel 340 defines a side cross section on a perpendicular (top-to-bottom) plane through the axis 360 that is substantially arcuate. The radius of this upwardly sloping arc is highly variable. Likewise, the arc need not be a portion of a circle, but can be another geometric curved shape. The heel 340 of this embodiment is also arced along the cross section taken perpendicularly through the axis, defining an approximate radius R (FIG. 3) that decreases continuously from the shaft junction 350 to the point 362. Moreover, as viewed from the top (FIG. 6), the needle tip defines a substantially triangular shape. In alternate embodiments the linear sides of the triangle can be substituted with curved sides or another appropriate geometry. Overall, the three dimensional heel shape is suggestive of a boat prow, but without a sharp keel so as to blunt the effects of contact with the vessel's back wall.

As also depicted in FIGS. 3-6, the needle side port 370 and aligned catheter notch 440 each appear as a rectangular shape. In alternate embodiments, the port can be a square, oval or other suitable shape, located to ensure that flashback occurs when the catheter is appropriately positioned. In general, the shape of the port/notch can be influenced by the manufacturing techniques used to form the enclosed tip distal end and point.

Figure 7:
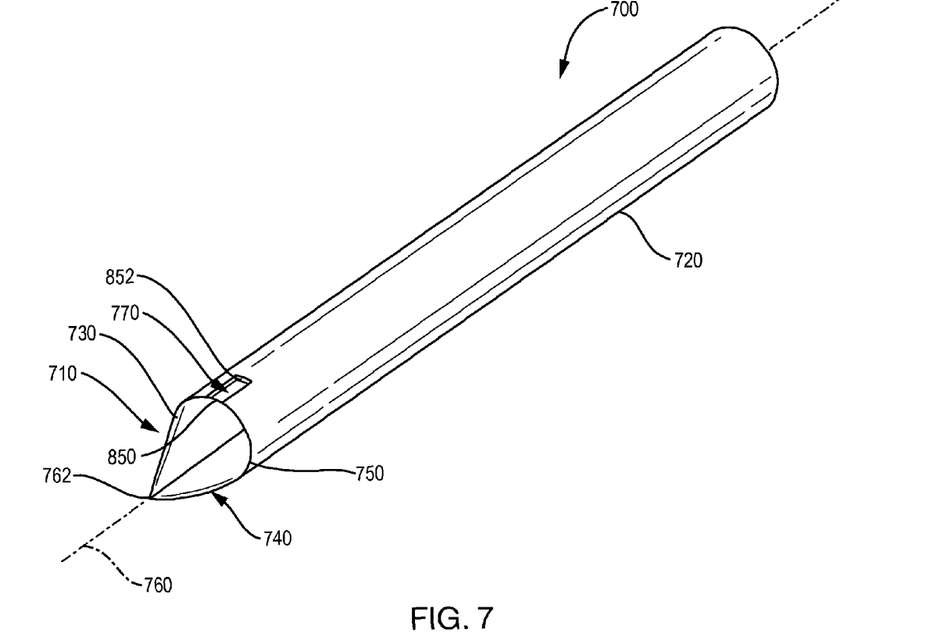
FIG. 7 is a perspective view of an insertion needle according to an illustrative embodiment including a tip having a centered point with a proximally positioned port located along the shaft side adjacent to the tip to help prevent flashback prior to full insertion and an opposing second side shaped with a rounded surface to minimize damage due to over-insertion.

Reference is now made to FIGS. 7-10, which show an alternate embodiment of an insertion needle and catheter embodiment according to this invention. The needle 700, shown alone in FIG. 7 is similar in construction to the needle 300 shown and described with reference to FIG. 3, above. It contains a tip 710, connected to a cylindrical shaft 720 at a circular joint junction 750 in a plane generally perpendicular to the longitudinal axis 760 through the center of the shaft 720. The tip defines a flattened or beveled upper surface 730 and an opposing curved, bottom heel surface 740. The dimensions and sizes of these surfaces can be similar to those (i.e. respective surfaces 3330, 340) of the tip 310. Alternatively the tip surfaces can have alternate dimensions that function within the general teachings of the embodiments herein. The surfaces terminate distally at a sharp point 762 located approximately along the axis 760 that facilitates easy insertion through tissue. Note that in the various embodiments herein, the length of the tip in highly variable and depends upon the diameter of the needle shaft 720. In an embodiment, the tip length from junction to point length can be approximately 1-2 times (more or less) that of the diameter.

In this embodiment the port 770 includes a distal edge 850 that is located approximately at the junction 750 between the straight shaft 720 and tapered tip 710. The precise location of the distal edge 850 of the port can be proximal or distal of the junction 750. In general, this embodiment locates all or substantially all of the port on the side, generally adjacent to the junction. In this manner, the entire tip is inserted through the vascular wall before flashback can occur. By locating the port along the shaft side, the formation of the tip 710 can entail a more solid interior (e.g. the tip is built up with plastic deformation and welding, or the tip can be a separate solid component attached to a notched end of a hollow needle shaft.

Figure 8:
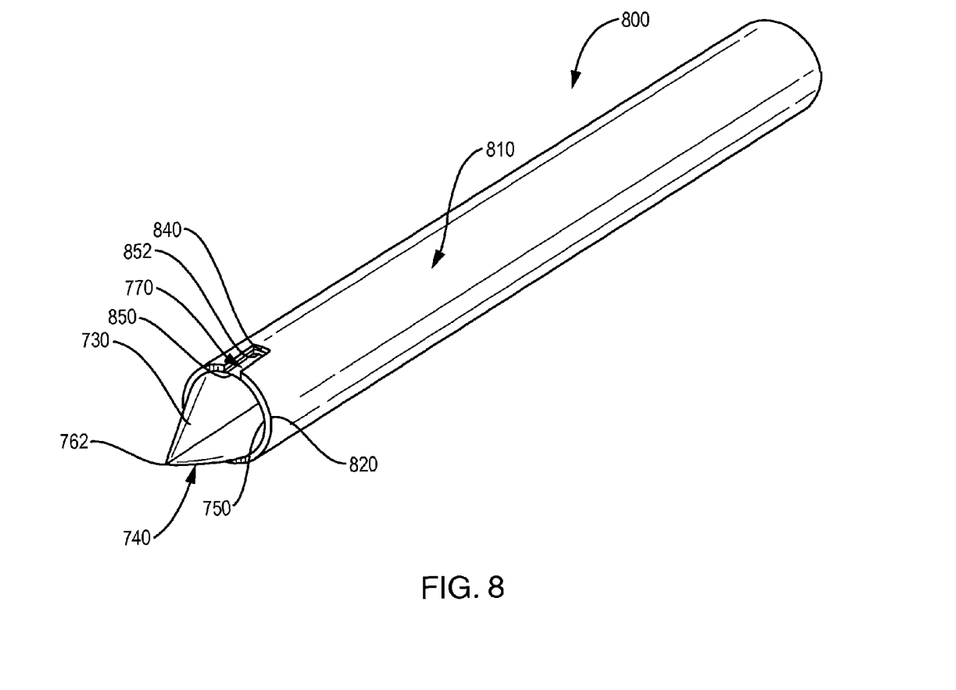
FIG. 8 is a perspective view of a catheter and needle arrangement according to an illustrative embodiment, employing the needle of FIG. 7 and including an overlying catheter having a distal end that extends along the cylindrical needle shaft up to the taper on the needle tip and includes a slot approximately aligned with the needle port.
Figure 9:
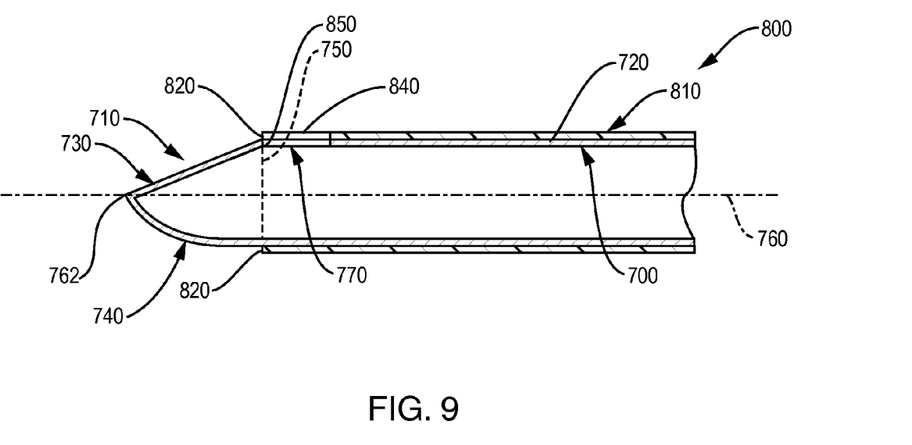
FIG. 9 is a partial side cross section of the distal portion of the needle and catheter arrangement of FIG. 8.
Figure 10:
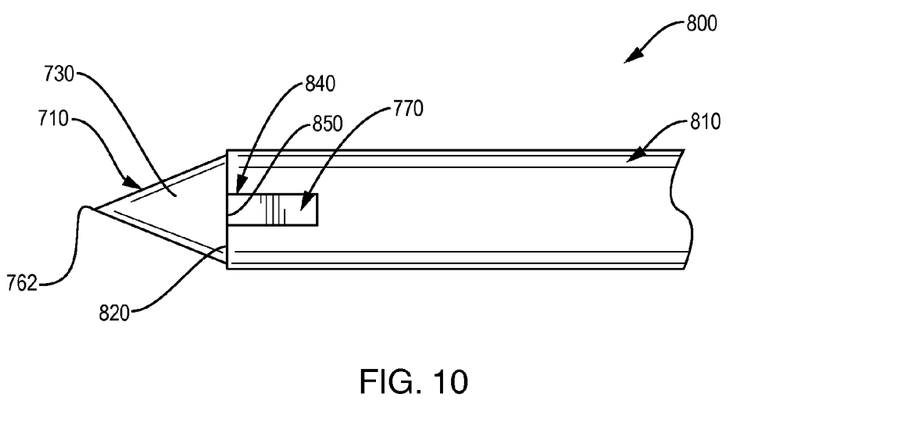
FIG. 10 is a partial top view of the distal portion of the needle and catheter arrangement of FIG. 4.

As shown further in FIGS. 8-10, the complete needle and catheter arrangement 800 includes an overlying catheter 810 similar in material and construction to the catheter 410 described above. The catheter extends proximally along the underlying needle shaft 700 to a distal end 820. In this embodiment, the catheter's distal end 820 is approximately aligned with the tip-to-shaft junction 750, thereby alleviating the need for a distal tapered section (e.g. section 422 in FIG. 4) that rides onto the needle tip. The distal end 820 includes a notch 840 that is approximately aligned with the needle port 770 so as to leave the port unobstructed for flashback. The overall distal-to-proximal length of the port 770 and notch 840 is highly variable. In various embodiments, this length can be approximately 30-100 percent of the length of the tip, but other length dimensions are expressly contemplated. Likewise, the maximum width of the notch (perpendicular to the distal-to-proximal length) in the various embodiments herein is highly variable. The width can be approximately 20-100 percent of the length in various embodiments. This width should be sufficient to allow appropriate flow of blood, but not compromise the structural strength and/or rigidity of the needle or catheter tip. Moreover, as discussed above, the shape of the notch is highly variable. It can be square or rectangular as shown, or another polygonal and/or curvilinear shape, such as ovular or trapezoidal.

Figure 11:
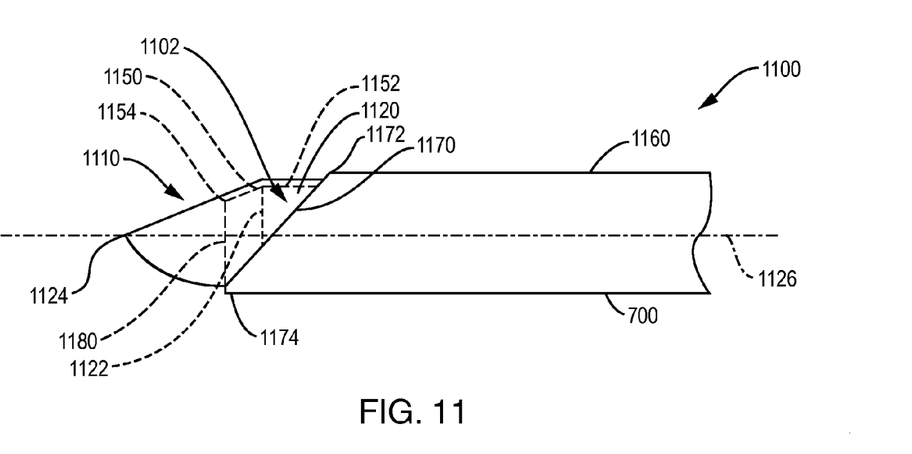
FIG. 11 is a partial side view of the distal portion of a catheter and needle arrangement according to an alternate embodiment.

Another illustrative embodiment of the insertion needle and catheter arrangement 1100 is shown in FIG. 11. In this embodiment, the needle 1102 includes a shaft 1120 and tip 1110 interconnected by a circular junction 1122 as described generally in the embodiments above. The tip 1110 includes beveled top surface 1130 and opposing curved heel 1140 as also described above. A tip, likewise, tapers distally into a sharp point 1124 residing approximately on or adjacent to a central longitudinal axis 1126 of the shaft 1120. The top surface 1130 of the needle 1102 and the adjacent portion of the shaft 1120, near the junction 1122 include a port 1150 in accordance with an embodiment of this invention. The port 1150 can be located substantially entirely on the beveled surface or substantially entirely on the shaft 1120 in alternate embodiment. The catheter 1160, constructed in accordance with various embodiments of this invention includes a distal end 1170 defining a beveled (chisel-like) tip, which extends distally between a top side 1172, adjacent the proximal edge 1152 of the port 1150 and a bottom side 1174 adjacent the heel 1140. In particular, the top side 1172 of the catheter tip is located at or near the proximal edge of the port 1150 in this embodiment. Likewise, the bottom side 1174 is located approximately in line (dashed line 1180) with the distal edge 1154 of the port 1150. In this manner, when the needle passed through the vascular wall, at a conventional insertion angle, at least a portion of the bottom side will also penetrate and pass into the vessel before the port is in communication with the bloodstream. Thus, if threading occurs prematurely, the beveled distal end 1170 of the catheter (at least partially inserted) will serve to guide the remainder of the catheter into the vessel as it is driven distally thereinto. It should be clear that the angle of the catheter distal end 1170, length of the port 1150, and placement of the port can be varied.

Reference is now made to FIGS. 12-15, which detail an exemplary insertion procedure employing a needle and catheter arrangement according to an embodiment of this invention. In the depicted example the illustrative arrangement 400 is employed. However, the insertion techniques used and outcomes achieved are similar for any of the other illustrative embodiments shown or contemplated herein.

Figure 12:
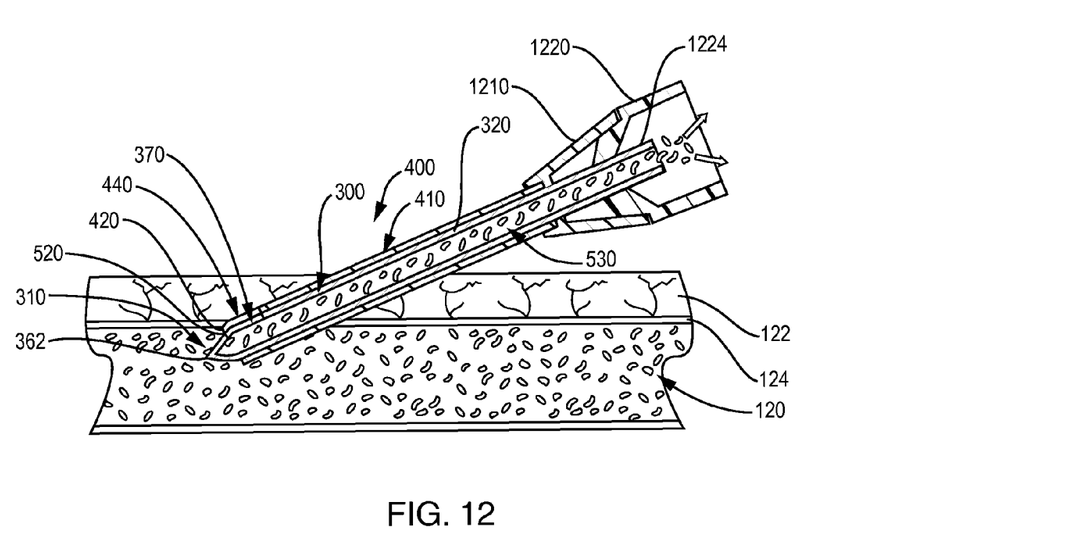
FIG. 12 is a side cross section showing, by way of example, the insertion of the needle and catheter of the embodiment of FIG. 4 into an exemplary vessel wherein flashback occurs only after the catheter has been fully inserted into the vessel.

As shown in FIG. 12, the needle and catheter arrangement 400, including the catheter 410 and underlying needle 300 with tip 310 has been inserted at an appropriate angle by a practitioner through the skin layer 122 and vascular wall 124, into the exemplary blood vessel 120. As shown, the catheter 410 is interconnected with a conventional proximal fitting 1210 for interconnecting an IV tube or other device. The fitting 1210 nests with a more-proximal flash chamber/fitting 1220, that is fixedly connected to the proximal end 1224 of the needle 300 and allows the needle to be slidably separated from the catheter 410 as described further below. The needle tip 310 has just pierced the vascular wall 124 and now resides fully in the vessel 120, in communication with the bloodstream. The distal end 420 of the catheter, which overlies the tip 310 and needle shaft 320 is also fully within the vessel, although minimally. The needle tip port 370 and catheter distal notch 440 are concurrently exposed, in part, to the bloodstream. At this moment, the blood flows up the needle lumen 530 as shown, and appears at the flash chamber 1220. The practitioner thus receives his or her indication that the needle and catheter has been implanted—and in fact, the catheter is sufficiently located within the vessel 120 to begin threading.

Figure 13:
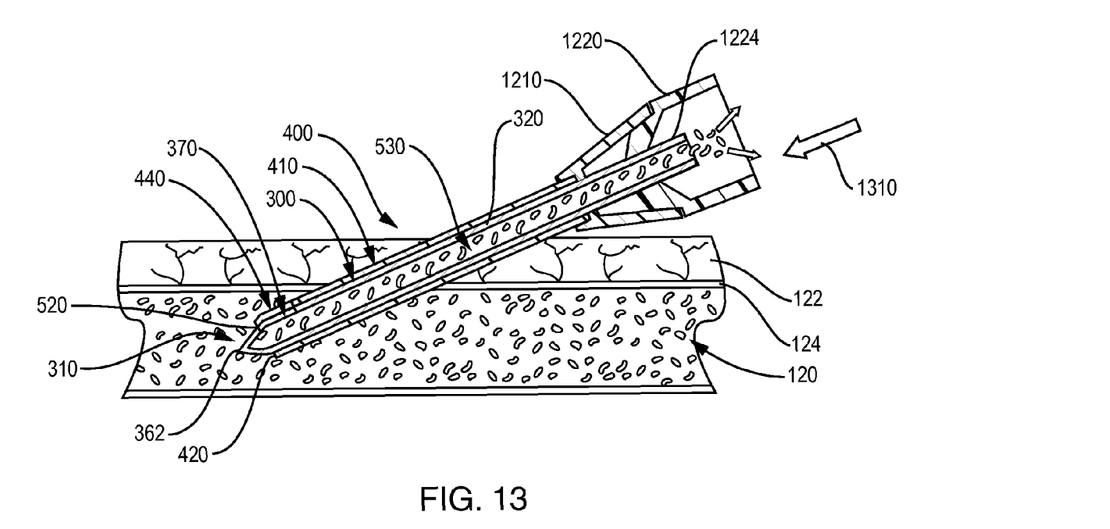
FIG. 13 is a side cross section showing the further insertion of the needle and catheter arrangement of the embodiment of FIG. 4 into a more desired, centralized location in the vessel, with the point of the tip still safely proximate of the vessel's back wall.
Figure 14:
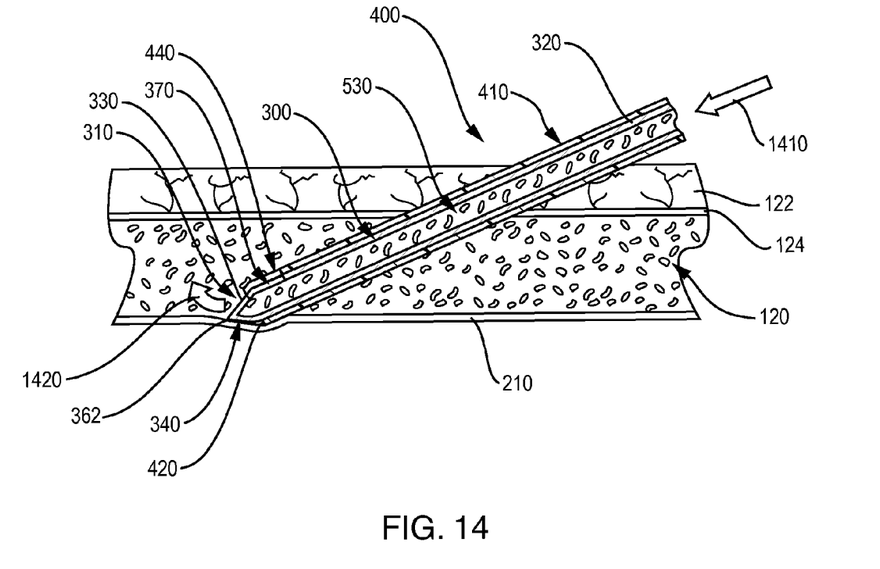
FIG. 14 a side cross section showing the over-insertion of the needle and catheter arrangement of the embodiment of FIG. 4 into contact with the back wall of the vessel, and wherein the placement of the point and curved geometry of the tip's second side reduces the risk of damage to the vascular wall.

As shown in FIG. 13, the practitioner may continue to insert (arrow 1310) the needle and catheter arrangement 400 in accordance with conventional best practices an extra few millimeters to achieve an assured positioning of the distal end 420 of the catheter well within the volume of the vessel. The point 362 of the tip 310 is still sufficiently remote from the back wall 210 of the vessel 120 so that the risk of contacting the wall is minimal.

Where the practitioner over-inserts (distally) the needle and catheter arrangement (arrow 1410) as shown in FIG. 14, the geometry of the heel, and more-axial placement of the sharp tip point 362 clearly reduce the risk of damage to the back wall 210 of the vessel 120. The back wall 210 has been slightly depressed by the engagement with the tip 310—and more particularly the heel 340. The placement of the point 362 avoids a direct puncturing of the wall 210, and the associated damage. The curved geometry of the heel, likewise, blunts any damage to the wall and aids in redirecting the tip along the wall in an upwardly curving direction (curved arrow 1420) as shown. So long as the practitioner avoids unreasonably light insertion force and/or an unconventionally steep angle of insertion, the tip should minimize the risk of undesirable damage to the vessel and harm to the patient.

Figure 15:
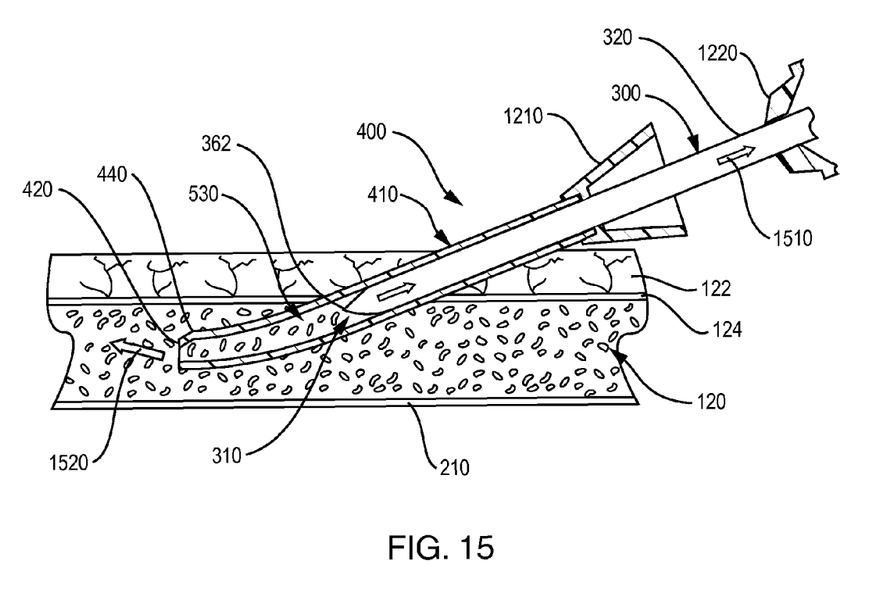
FIG. 15 is a side cross section of the threading of the catheter into the vessel with respect to the needle in the arrangement of the embodiment of FIG. 4.

As shown in FIG. 15, the catheter 410 is now safely threaded into the vessel as a result of the successful insertion in accordance with any of FIGS. 12-14. The needle 300 and its associated shaft 320 and tip 310 are withdrawn proximally (arrow 1510) through the lumen 1530 of the catheter, while the catheter 410 is biased (arrow 1520) distally into a final position within the vessel. The catheter proximal fitting 1210 and needle proximal fitting 1220 are separated from each other as shown to facilitate this motion—typically being grasped by opposing hands of the practitioner. Once the needle is fully withdrawn, the exposed proximal end of the catheter 410 can be secured with tape or another mechanism for connection of the fitting 1210 with an appropriate tubing end or other device.

Figure 16:
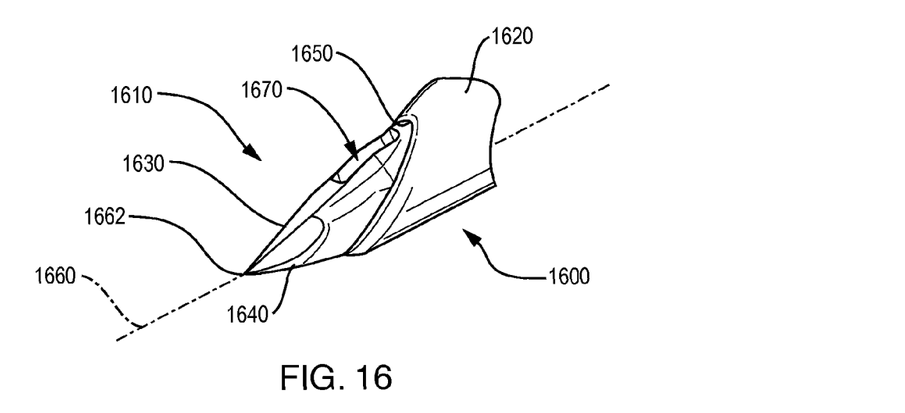
FIG. 16 is a partial perspective view of an insertion needle according to an alternate embodiment including a tip having a centered point with a proximally positioned port located along both the tip and adjacent shaft side to help prevent flashback prior to full insertion and an opposing second side shaped with a rounded surface to minimize damage due to over-insertion.
Figure 17:
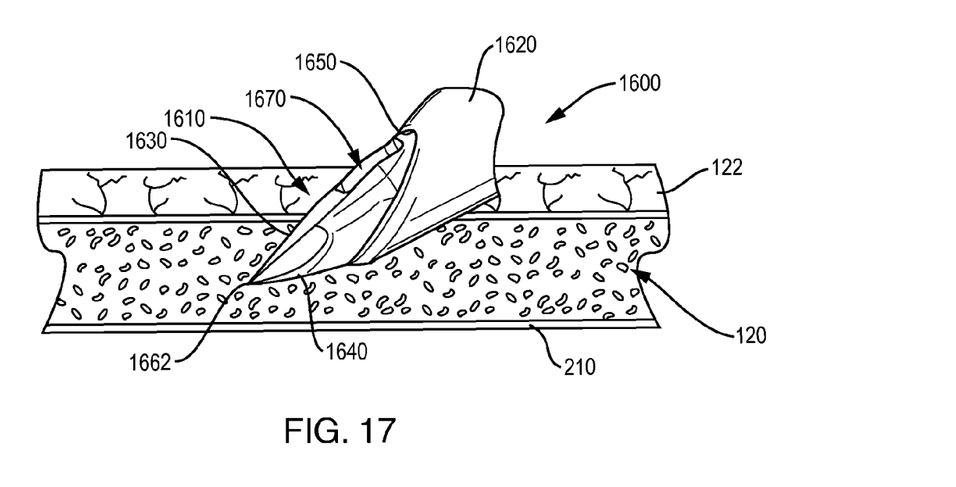
FIG. 17 is a perspective view showing, by way of example, the insertion of the needle of FIG. 16 into an exemplary vessel wherein flashback occurs only after the needle has been fully inserted into the vessel.
Figure 18:
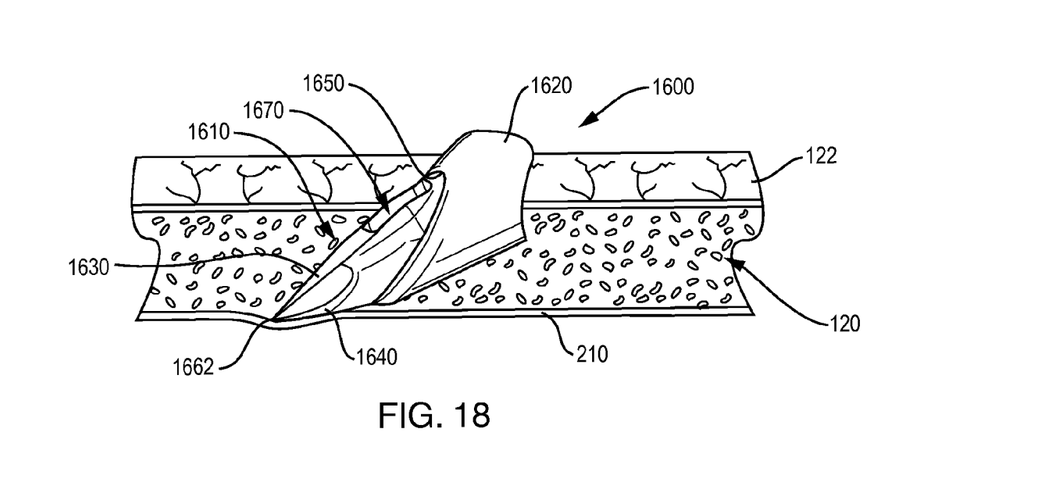
FIG. 18 is a perspective view showing the over-insertion of the needle of FIG. 16 into contact with the back wall of the vessel, and wherein the placement of the point and curved geometry of the second side of the tip reduces the risk of damage to the vessel.

Reference is now made to FIGS. 16-18, showing an illustrative embodiment of the needle assembly 1600 shown as a three-dimensional view of the needle and overlying catheter arrangement. The depicted needle assembly 1600 includes a needle tip 1610 and a catheter 1620 overlying a shaft (not shown) of the needle 1600. It is noted that the needle tip 1610 and proximal needle shaft (not shown but underlying the catheter 1620) can be employed without a catheter in alternate embodiments, but are shown with an overlying catheter for descriptive purposes. The needle tip 1610 has a first (upper) side 1630 and an opposing (bottom) side 1640 defining a generally curved heel. The tip 1610 in this embodiment interconnects with a straight, cylindrical shaft section having the overlying catheter 1620 at a relatively circular junction 1650. The circular junction 1650 resides in a plane that is approximately perpendicular to the longitudinal (axis of elongation) 1660 taken long the center (cross sectional center/centroid) of the shaft 1620.

The tip 1610 includes a distal-most sharp enclosed point 1662 that resides approximately within the axis 1660 in this embodiment. It is contemplated, as with the other embodiments discussed herein, that in alternate embodiments the point 1662 may reside below or above the axis 1660. However, the point 1662 should be located so as to generate an upwardly curved surface 1640 of the tip 1610 that operates to reduce potential damage to the vascular wall. As shown in greater detail in FIG. 18, the curved bottom surface 1640 of the tip 1610 reduces the risk of puncturing the vascular wall 210.

It is noted that the needle assembly 1600 is shown and described as including an overlying catheter in an illustrative embodiment of the invention. However, it is expressly contemplated that the needle structure itself is readily applicable to any medical treatment or method employing a needle free of an overlying catheter. The structure provides improved flashback readings to a user of the needle structure, desirable for not only catheter application, but any intravascular application, such as simple blood draws. In this manner, the needle is employed to determine that the orifice is fully within the vein, prior to drawing in the blood. The needle structure of this embodiment further reduces the risk of over-penetrating, and possibility of puncturing, a vessel wall, due to the curved heel of the needle. Where used in application as a "standalone" needle the proximal end can be fixedly or removably (using, for example a Luer fitting) attached to a syringe body or other fluid-draw/delivery device.

The needle assembly 1600 includes a side orifice or port 1670 that is located on an upper side of the needle, opposite the curved heel, and proximally offset from the distal-most sharp enclosed point 1662. The side port 1670 is shown on a first (upper) side of the needle tip 1610, however it is expressly contemplated that the port 1670 can be displaced at a greater distance from the enclosed point 1662, on an upper side of the needle shaft (not shown), depending on the particular application for which the needle assembly 1600 is constructed and arranged. The port 1670 is in fluid communication with the blood vessel once inserted into a blood vessel, as shown and described with reference to FIGS. 17 and 18.

FIGS. 17 and 18 detail an exemplary insertion procedure employing the needle arrangement according to an illustrative embodiment of this invention. In the depicted example the illustrative arrangement 1600 is employed. As shown in FIG. 17, the needle assembly 1600, including the needle 1610 and overlying catheter 1620, has been inserted at an appropriate angle by a practitioner through the skin layer 122, into the exemplary blood vessel 120. As shown, the needle tip 1610 has just pierced the skin 122 and vascular wall and now resides fully in the vessel 120, in communication with the bloodstream. The distal end of the catheter 1620, which overlies the tip 1610 and the needle shaft is also fully within the vessel, although minimally. At this moment, the blood flows up the needle lumen (as shown in FIG. 12 and described hereinabove) and flashback occurs, indicating the needle resides fully within the blood vessel.

As shown in FIG. 18, where a practitioner inadvertently over-inserts (distally) the needle assembly 1600, the geometry of the heel, or second side of the tip 1640, and more-axial placement of the sharp enclosed point 1662 clearly reduce the risk of damage to the back wall 210 of the blood vessel 120. The back wall 210 is shown slightly depressed by the engagement with the tip 1610, and more particularly the heel 1640. However, the curved geometry of the heel blunts any damage to the wall and aids in redirecting the tip along the wall in an upwardly curving direction. It should be clear that the length of the tip region and the relative curvature of the heel are highly variable. These can be optimized for the particular size vessel into which the needle will be inserted, as well as the anticipated angle of insertion. Optimization can be accomplished using empirical data or by trial and error experimentation, using varying dimensions and determining the results. In any case, it should be clear that needle design of the illustrative embodiments provides an effective mechanism for ensuring full insertion of the needle into a vessel, and reduction of damage due to over-penetration.

The foregoing has been a detailed description of illustrative embodiments of the invention. Various modifications and additions can be made without departing from the spirit and scope of this invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. For example, the specific geometry of geometry of the needle tip is highly variable. It is generally contemplated that the tip include a proximally relocated port with an overlying catheter distal end that, at least partially, distally overlaps the port in a manner that still allows the port to transmit blood during flashback—so that insertion of the needle and catheter arrangement provided flashback only after the catheter element is sufficiently within the target blood vessel. Likewise, the tip includes a pointed end for ease of insertion and a heel, opposite the port-containing side, is curved upwardly to place the point closer to the longitudinal axis and reduce the effects of damage against the back wall of the vessel due to over-insertion. Additionally, while an upwardly curved heel is described, the term "curved" should be taken broadly to include a variety of upwardly sloped surface geometries (e.g. a segmented geometry) that relocate the position of the distal-most sharp needle point and reduce the risk of vessel wall damage. Also, the terms "proximal," "distal," "top," "bottom," "vertical," "horizontal," and the like, as used herein, should be considered as conventions only. Accordingly, this description is meant to be taken only by way of example, and not to otherwise limit the scope of this invention.

What is claimed is:

1. A needle and catheter assembly for insertion into a blood vessel comprising:
   a needle having a needle shaft and a needle tip extending distally from a proximal shaft junction, the needle tip defining a distal-most sharp point that is enclosed at a needle distal end;
   a side port in fluid communication with a lumen of the needle shaft located on a first side adjacent to the shaft junction, such that a surface of the side port extends continuously from a portion of the needle tip, through the shaft junction, and onto an adjacent portion of the needle shaft;
   an upwardly curved heel on the needle tip along a second side opposite the first side that extends from the shaft junction to the distal-most sharp point and thereby locates the point adjacent to a longitudinal axis of the shaft; and
   a catheter overlying the needle and having a catheter distal end located with respect to the needle tip so that at least a portion of the catheter distal end extends distally past the shaft junction with the side port being unobstructed by the catheter distal end so as to maintain the fluid communication with the lumen.

2. The needle and catheter assembly as set forth in claim 1 wherein the catheter distal end includes a notch, formed within a surface thereof that is approximately aligned with the side port.

3. The needle and catheter assembly as set forth in claim 2 wherein the side port is located at least in part on the tip along a beveled surface that extends distally toward the distal-most sharp point and the catheter distal end includes a conforming taper on which the notch is located that conforms to a shape of the heel and the beveled surface.

4. The needle and catheter assembly as set forth in claim 3 wherein the side port extends proximally from the beveled surface on to an adjacent portion of the needle shaft.

5. The needle and catheter assembly as set forth in claim 1 wherein the catheter distal end comprises a beveled distal edge with a top side of the beveled distal edge being more proximal and adjacent to a proximal edge of the side port and an opposing bottom side of the beveled distal edge being more distal along the longitudinal axis.

6. The needle and catheter assembly as set forth in claim 5 wherein the bottom side of the beveled distal edge is aligned approximately with respect to a distal edge of the side port along the longitudinal axis.

7. A needle for insertion into a blood vessel comprising:
   a needle shaft and a needle tip extending distally from a proximal shaft junction, the needle tip defining a distal-most sharp enclosed point at a needle distal end;
   a side port located on a first side of the needle, the side port being in fluid communication with a lumen of the needle shaft to determine when the needle tip resides fully in the blood vessel, such that a surface of the side port extends continuously from a portion of the needle tip, through the shaft junction, and onto an adjacent portion of the needle shaft; and
   an upwardly curved heel on a second side of the needle, opposite the first side of the needle, that extends from the shaft junction to the distal-most sharp enclosed point, wherein the upwardly curved heel prevents over-insertion of the needle in the blood vessel by protecting the distal-most sharp enclosed point from puncturing a back wall of the blood vessel.

8. The needle as set forth in claim 7 wherein the side port of the needle is offset from the distal-most sharp enclosed point such that flashback occurs when the needle is fully inserted into the blood vessel.

9. The needle as set forth in claim 7 wherein the side port is located on an upper side of the needle shaft such that flashback occurs when the needle tip resides fully in the blood vessel.

10. The needle as set forth in claim 7 further comprising a catheter overlying the needle, the catheter having a catheter distal end locate proximate to the needle tip such that at least a portion of the catheter distal end extends distally past the side port.

11. A medical treatment method comprising the steps of:
    inserting a needle into a blood vessel of a human, the needle having a needle shaft and a needle tip extending distally from a proximate shaft junction, wherein the needle tip defines a sharp enclosed point at a needle distal end that punctures through and into the blood vessel, the needle including a side port that extends continuously from a portion of the needle tip, through the proximate shaft junction, and onto an adjacent portion of the needle shaft; and
    observing flashback when the needle tip resides fully in the blood vessel as occurring in response to fluid communication of a the side port on the needle with the blood vessel, thereby indicating that the needle tip resides fully in the blood vessel.

12. The medical treatment method as set forth in claim 11 further comprising:
    providing a catheter that overlies the needle and, after the step of determining flashback has occurred, removing the needle to thereby enable threading of the catheter into the blood vessel.

13. The medical treatment method as set forth in claim 12 further comprising:
    threading the catheter when the needle tip resides fully in the blood vessel to secure the catheter within the blood vessel; and
    removing the needle after the catheter has been threaded to thereby leave the catheter in the blood vessel.

14. The medical treatment method as set forth in claim 11 including, when directing the needle against an opposing back wall of the blood vessel with respect to a punctured wall thereof, engaging the opposing back wall of the blood vessel with a curved heel of the tip so as to minimize damage to the back wall of the blood vessel.

* * * * *